United States Patent
Swift

(10) Patent No.: US 6,448,220 B1
(45) Date of Patent: *Sep. 10, 2002

(54) FRAGRANCE COMPOUND

(75) Inventor: Karl Andrew Dean Swift, Ashford (GB)

(73) Assignee: Quest International B.V., Naarden (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,450

(22) Filed: Mar. 30, 1999

(30) Foreign Application Priority Data

Mar. 30, 1998 (EP) .............................. 98302422

(51) Int. Cl.[7] .................. A61K 7/46; C07C 49/105; C07C 49/00

(52) U.S. Cl. ..................... 512/23; 512/22; 512/25; 568/376; 568/377; 568/367; 568/303

(58) Field of Search ................... 568/376, 377, 568/367, 303; 512/22, 23, 24, 25, 26, 27

(56) References Cited

U.S. PATENT DOCUMENTS 3,268,589 A * 8/1966 Rowland ................... 568/341

FOREIGN PATENT DOCUMENTS

| DE | 36 40 591 A1 | 6/1988 |
|---|---|---|
| FR | 1.467.386 | 4/1967 |
| WO | WO 93/03012 | 2/1993 |

OTHER PUBLICATIONS

Beilstein Abstract, CAS Reg. Nr. 1822–37–3.
Beilstein Abstract, CAS Reg. Nr. 1822–39–5.
Beilstein Abstract, Beilstein Reg. Nr 7198680.
Beilstein Abstract, Beilstein Reg. Nr 7198681.

(List continued on next page.)

*Primary Examiner*—Gabrielle Brouillette
*Assistant Examiner*—Monique T. Cole
(74) *Attorney, Agent, or Firm*—Morgan, Lewis & Rockius LLP

(57) ABSTRACT

The novel ketones having the structure

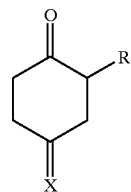

in which R is H or an alkyl group and X is a hydrocarbon group having between 4 and 12 carbon atoms, the ring being saturated or unsaturated, excluding 4-(1-ethylpropylidene)-1-cyclohexanone, 4-cyclohexylidene-1-cyclohexanone, 4-butylidene-1-cyclohex-2-enone, 4-(1-ethylpropylidene)-1-cyclohex-2-enone, 4-(2-methylpropylidene)-1-cyclohexanone, 4-cyclohexyliden-2-cyclohexen-1-one, 4-(1,5-dimethyl-4-hexenylidene)-1-cyclohexanone, 4-[4-(cyclohexyliden)cyclohexyliden]-1-cyclohexanone, 4-[4-(tert-butyl)cyclohexyliden]-1-cyclohexanone, 4-[-(cyclohexyl)cyclohexyliden]-1-cyclohexanone, 4-(2-isopropyl-5-methylcyclohexyliden)-2-cyclohexen-1-one and 4-(3-phenylpropylidene)-1-cyclohex-2-enone exhibit interesting odor characteristics, generally aldehydic in nature, and so find use in perfumes and in perfumed products.

11 Claims, 1 Drawing Sheet

OTHER PUBLICATIONS

Beilstein Abstract, CAS Reg. Nr 61365–71–7.
Humphreys et al, J. Chem. Soc., Perkin Trans. (XP–002075192) pp. 24–33 (1978).
Vig et al, J. Indian Chem. Soc., 52(7):614–616 (Jul. 1975).
Hoogesteger et al. J. Org. Chem., 60(14):4375–4384 (1995).

Nidy et al., Synthesis, 90(11):1054–1056 (Nov. 1990).

Flisak et al., J. Am. Chem. Soc., 112(20):7299–305 (1990).

Gesson et al., Nouv. J. Chim., 1(6):511–20 (Jun., 1977).

* cited by examiner

FRAGRANCE COMPOUND

FIELD OF THE INVENTION

This invention concerns novel fragrance compounds, and their use in perfumes and perfumed products.

SUMMARY OF THE INVENTION

In one aspect the invention provides a ketone having the structure

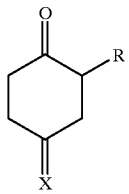

Figure 1:
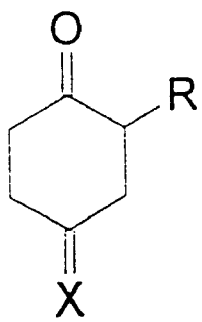

(as shown in FIG. 1) in which R is H or an alkyl group and X is a hydrocarbon group having between 4 and 12 carbon atoms, the ring being saturated or unsaturated, excluding 4-(1-ethylpropylidene)-1-cyclohexanone, 4-cyclohexylidene-1-cyclohexanone, 4-butylidene-1-cyclohex-2-enone, 4-(1-ethylpropylidene)-1-cyclohex-2-enone, 4-(2-methylpropylidene)-1-cyclohexanone, 4-cyclohexyliden-2-cyclohexen-1-one, 4-(1,5-dimethyl-4-hexenylidene)-1-cyclohexanone, 4-[4-(cyclohexyliden)cyclohexyliden]-1-cyclohexanone, 4-[4-(tert-butyl)cyclohexyliden]-1-cyclohexanone, 4-[4-(cyclohexyl)cyclohexyliden]-1-cyclohexanone, 4-(2-isopropyl-5-methylcyclohexyliden)-2-cyclohexen-1-one and 4-(3-phenylpropylidene)-1-cyclohex-2-enone.

The specifically excluded materials, namely 4-(1-ethylpropylidene)-1-cyclohexanone, 4-cyclohexylidene-1-cyclohexanone, 4-butylidene-1-cyclohex-2-enone, 4-(1-ethylpropylidene)-1-cyclohex-2-enone, 4-(2-methylpropylidene)-1-cyclohexanone, 4-cyclohexyliden-2-cyclohexen-1-one, 4-(1,5-dimethyl-4-hexenylidene)-1-cyclohexanone, 4-[4-(cyclohexyliden)cyclohexyliden]-1-cyclohexanone, 4-[4-(tert-butyl)cyclohexyliden]-1-cyclohexanone, 4-[4-(cyclohexyl)cyclohexyliden]-1-cyclohexanone, 4-(2-isopropyl-5-methylcyclohexyliden)-2-cyclohexen-1-one and 4-(3-phenylpropylidene)-1-cyclohex-2-enone, are known materials but they do not have fragrance properties that are interesting or attractive. 4-(1-ethylpropylidene)-1-cyclohexanone is disclosed in Inhoffen H. H. et al., Justus Liebigs Ann. Chem., (1964), 674, p28–35; 4-cyclohexylidene-1-cyclohexanone is disclosed in Hoogesteger F. J. et al., J. Org. Chem., (1995), 60(14), p4375–4384 and Hoogesteger, F. J. et al., J. Chem. Soc. Perkin Trans. 2, (1996), p2327–2334; 4-butylidene-1-cyclohex-2-enone is disclosed in Flemming I. et al., Tetrahedron Letters, (1979), p3209–3212; 4-(1-ethylpropylidene)-1-cyclohex-2-enone is disclosed in Inhoffen H. H. et al., Justus Liebigs Ann. Chem., (1964), 674, p28–35; 4-(2-methylpropylidene)-1-cyclohexanone is disclosed in WO 93/03012 in Example 6; 4-cyclohexyliden-2-cyclohexen-1-one is disclosed in Humphries D J et al, J. Chem. Soc. Perkin Trans. 1; 1978; p24–33 as compound 14; 4-(1,5-dimethyl-4-hexenylidene)-1-cyclohexanone is disclosed in Vig OP et al, J. Indian Chem. Soc.; 1975; vol 52, p 614–616 as compound IX; 4-[4-(cyclohexyliden) cyclohexyliden]-1-cyclohexanone and 4-[4-tert-butyl) cyclohexyliden]-1-cyclohexanone are disclosed in Hoogester F J et al, J. Org. Chem.; 1995; p4375–84 as compounds 14(2) and 21(1), respectively; 4-[4-(cyclohexyl) cyclohexyliden]-1-cyclohexanone is disclosed in Nidy EG et al, Synthesis; 1990; p1053–6 as compound 9; 4-(2-isopropyl-5-methylcyclohexyliden)-2-cyclohexen-1-one is disclosed in Flisak J R et al, J. Am. Chem. Soc.; 1990; p7299–7305 as compound 14b; and 4-(3-phenylpropylidene)-1-cyclohex-2-enone (cis and trans isomers) are disclosed in Gesson J P et al, Nouv. J. Chim., Vol. 1(6), p 511–20 as compounds 22a and 22b.

In a further aspect the invention thus provides a ketone having the structure

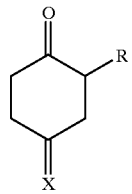

(as shown in FIG. 1) in which R is H or an alkyl group and X is a hydrocarbon group having between 4 and 12 carbon atoms, the ring being saturated or unsaturated, the ketone having fragrance properties.

The term "fragrance properties" is used to mean a discernible odour at normal room temperature (about 25° C.) that is generally regarded as interesting, pleasant or attractive.

For brevity and simplicity, materials in accordance with the invention will be referred to herein as "the ketone", "the novel ketone" or "the ketones of the invention".

The ketones of the invention exhibit interesting fragrance properties or odour characteristics, generally aldehydic in nature, and so may be used as such to impart, strengthen or improve the odour of a wide variety of products, or it may be used as a component of a perfume (or fragrance composition) to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or any product for which an agreeable odour is indispensable or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can be advantageously combined with a ketone according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with a ketone according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzyl-carbinol, trichloromethyl-phenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)-propanal, 2,4-dimethyl-cyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes which contain a ketone according to the invention are, for example: ethanol, isopropanol, diethyleneglycol monoethyl ether, dipropylene glycol, diethyl phthalate, triethyl citrate, isopropyl myristate, etc.

The quantities in which the ketone according to the invention can be used in perfumes or in products to be perfumed may vary within wide limits and depend, inter alia, on the nature of the product, on the nature and the quantity of the other components of the perfume in which the ketone is used and on the olfactive effect desired. It is therefore only possible to specify wide limits, which, however, provide sufficient information for the specialist in the art to be able to use the ketone according to the invention for his specific purpose. In perfumes an amount of 0.01% by weight or more of the ketone according to the invention will generally have a clearly perceptible olfactive effect. Preferably the amount is 0.1–80% by weight, more preferably at least 1%. The amount of the ketone according to the invention present in products will generally be at least 10 ppm by weight, preferably at least 100 ppm, more preferably at least 1000 ppm. However, levels of up to about 20% by weight may be used in particular cases, depending on the product to be perfumed.

In a further aspect the invention thus provides a perfume comprising a ketone of the invention in an olfactively effective amount.

The invention also covers a perfumed product comprising the ketone of the invention.

The hydrocarbon group X may be a straight chain, a branched chain or cyclic, and may include aromatic groups. Group X need not be attached to the main ring (ie the ring shown in FIG. 1) at the end of a chain: attachment at a point along the length of a chain is also possible. Group X may be saturated or unsaturated; it is currently preferred that group X is saturated. Straight chain attachments, particularly n-heptyl and n-pentyl, are currently preferred. Where group X is cyclic, X preferably comprises an alkyl ring having from 4 to 11 carbon atoms, optionally substituted with one or more groups at any position on the ring, the or each substituent comprising H or a lower alkyl group, ie methyl, ethyl or propyl, subject to group X having between 4 and 12 carbon atoms.

R is preferably H or a lower alkyl group, eg. methyl or ethyl.

The ketone preferably has no more than 18 carbon atoms in total. Thus, for example, where R is a methyl group, X preferably has no more than 11 carbon atoms.

The main ring is generally saturated, but may optionally be unsaturated. Where the main ring is unsaturated, X is preferably not cyclic.

Figure 2:
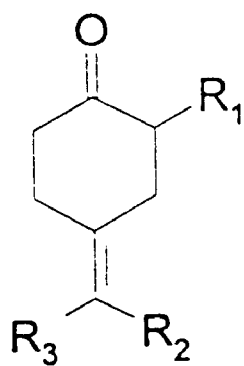
Figure 3:
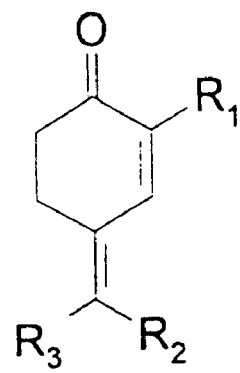

A large number of ketones in accordance with the invention have been prepared, generally by carrying out various different Wittig reactions on cyclohexane-1,4-dione mono-ethylene ketal. Table 1 gives details of a number of compounds of the general structure shown in FIG. 2 (having a saturated main ring) and also one compound of the general structure shown in FIG. 3 (having an unsaturated main ring), with three currently preferred compounds being identified for convenience by compound (or mol. ref.) numbers. In FIG. 3, $R_2$ and $R_3$ are preferably not cycloalkyl, cycloalkenyl or aromatic groups; instead $R_2$ and $R_3$ are preferably H, alkyl or alkenyl groups.

Figure 4:
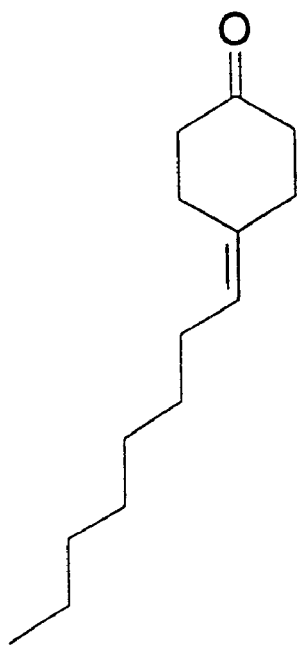
Figure 5:
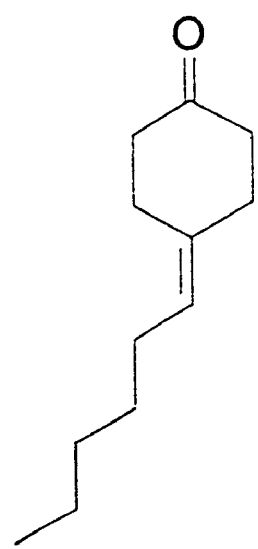
Figure 6:
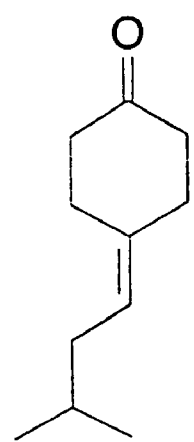

Of the compounds so far tested, those currently most favoured are compound I (R=H, X=n-octyl—FIG. 4) (4-octylidene-1-cyclohexanone), compound II (R=H, X=n-hexyl—FIG. 5) (4-hexylidene-1-cyclohexanone) and compound III (R=H, X=3-methylbutyl—FIG. 6) (4-(3-methylbutylidene)-1-cyclohexanone), all having a saturated main ring.

In a preferred aspect of the invention thus provides a ketone having the structure shown in FIG. 1, in which R is H, the main ring is saturated and X is a straight chain saturated hydrocarbon group having 6 or 8 carbon atoms, attached to the main ring by a double bond (compound I and compound II).

In another preferred aspect the invention provides a ketone having the structure shown in FIG. 1, in which R is H, the main ring is saturated and X is an isoamyl chain attached to the main ring by a double bond (compound III).

In a particularly preferred aspect the invention covers a ketone having the structure shown in FIG. 1, in which R is H, the main ring is saturated and X is a straight chain saturated hydrocarbon having 8 carbon atoms, attached to the main ring by a double bond (compound I).

Compound I has been shown to be effective as an aldehyde extender in soaps.

TABLE 1

| R1 | R2 | R3 | Mol. Ref. | Odour description Fresh | Odour description Dry | Synthesis route |
|---|---|---|---|---|---|---|
| H | n-Pentyl | H | II | Aldehydic, rose, fatty, marine | Marine, aldehydic, floral, rose | A |
| H | n-Butyl | H | | Fresh floral muguet, fatty, nitrile | Marine, aldehydic, muguet | A |
| H | n-propyl | H | | Rose, floral, aniseed, fatty | Aniseed, rose, floral | A |
| H | n-Hexyl | H | | Marine, mandarin, aldehydic | Mandarin, marine, aldehydic, ozone | A |
| H | n-heptyl | H | I | Fatty, aldehydic, marine | Marine, ozone, aldehydic, nitrile | A |
| H | n-Nonyl | H | | Aldehydic, fatty, marine, ozone | Aldehydic, fatty, marine, nitrile | A |
| H | n-Octyl | H | | Strong fatty, marine, aldehydic | Marine, aldehydic, ozone | A |
| H | n-Undecyl | H | | Ozone, marine, aldehydic | Ozone, marine, aldehydic | A |
| H | n-Propyl | Me | | Cuminic, citrus, spicy, weak aldehydic | Spicy, nitrile, weak aldehydic | B |
| Me | n-Pentyl | H | | Floral green, leafy, aldehydic | Marine, fresh, floral, green, aldehydic | D |
| H | 2-Methylpropenyl | H | | Ketonic, citral, lemongrass | Citral, lemon, lemongrass | A |
| H | Phenyl | H | | Fatty, green aldehydic, floral | Watery, aldehydic, muguet | A |
| H | 2-Methylpropyl | H | III | Rose, aldehydic, green, fruity | Green, herbal, aldehydic, fruity | A |
| H | n-Heptyl | H | ** | Green, citrus | Strong Citrus, aldehydic, nitrile | E |
| H | cyclopentylidene | | | Animalic, fruity, civet | Cresylic, animalic | B |
| H | cycloheptylidene | | | Woody, camphor | Odourless | B |
| H | cyclooctylidene | | | Woody, hay | Ortholate, woody, hay | B |
| H | cyclododecylidene | | | Odourless | Odourless | C |
| H | tricyclic group | | | Balsamic | Citrus, cumin | B |

TABLE 1-continued

| R1 | R2 | R3 | Mol. Ref. | Odour description | | Synthesis route |
|---|---|---|---|---|---|---|
| | | | | Fresh | Dry | |
| H | (cyclic structure) | | | Woody, cedar, fruity | Woody, cedar | B |
| H | (cyclopentylidene structure) | | | Sweet, honey | Sweet, phenolic | B |

** This compound has an unsaturated main ring, and so has the general structure shown in FIG. 3.

The invention will be further described, by way of illustration, in the following Examples and with reference to the accompanying figures, in which:

FIGS. 1 to 6 show the structure of ketones in accordance with the invention.

Ketones in accordance with the invention as set out in Table 1 were made by the following preparation routes.

General Experimental Section

Preparation Route A

Wittig Reaction on cyclohexane-1,4-dione Monoethylene Ketal

To a suspension of 1.05 equivalent of phosphonium salt (0.34 mole) suspended in THF (500 ml) was added 1.10 equivalent of n-butyllithium (2.5M in hexanes) (0.35 mole) slowly dropwise keeping the temperature below 20° C. with ice cooling. During the course of this addition the white/colourless suspension slowly dissolves to yield a deep red/clear solution. Once the addition is complete the solution was left at room temperature for a further 30 minutes. After this time a solution of 1 equivalent of cyclohexane-1,4-dione monoethylene ketal (0.32 mole) in THF (150 ml) is added slowly to the deep red solution. During the course of the addition the red colouration disappears to yield an orange solution containing a solid suspension. The temperature also increases to approximately 40° C. during the addition.

Once cooled to room temperature, water (150 ml) was added to dissolve the solid. The reaction mixture was shaken, and the organic layer was removed and concentrated in vacuo. The residue was partitioned between toluene (500 ml) and water (500 ml), and the toluene was further washed with brine (250 ml). The toluene was dried using a Dean and Stark, and then removed in vacuo to yield a viscous residue.

To the residue was added ether and the solid that precipitated was removed by filtration, and further washed with ice-cold ether. The combined filtrates were evaporate in vacuo, and to the residue that remained was added ice-cold pentane. Again, the solid that precipitated was removed by filtration, and washed with ice-cold pentane. The combined filtrates were evaporated in vacuo, and the residue that remained was distilled under reduced pressure.

Deprotection of the Ketal

The distillate (approx 20–30 g) from the Wittig reaction was poured into a mixture of concentrated HCl (160 ml) and butanone (40 ml), and shaken for a few minutes (until reaction complete by TLC). The solution was diluted with water (250 ml), and extracted twice with ether. The combined extracts were washed with water, saturated sodium bicarbonate, dried with magnesium sulphate, and concentrated in vacuo. The liquid residue remaining was distilled under vacuum to yield an almost colourless liquid product. Overall yields in the range of 30–50% based on cyclohexane-1,4-dionemonoethylene ketal.

Preparation Route B

Mc Murry Coupling of the Ketal with a Second Ketone

To a suspension of titanium III chloride (0.2 mole) in anhydrous THF (300 ml) was added lithium aluminium hydride (0.1 mole) in small portions! (Caution: A severe exotherm is encountered during this addition). After the exotherm the solution's appearance had changed from purple/black opaque to a black suspension.

To this suspension was added 1,4-cyclohexanedione monoethylene ketal (0.09 mole) and the other ketone (0.09 mole) in THF dropwise (No exotherm). Once complete the black solution was left overnight at room temperature.

The reaction was quenched with water dropwise (slight exotherm), and the clear black solution was poured into ether and extracted three times with brine. The clear organic fraction was dried using magnesium sulphate and evaporated in vacuo to yield a pale yellow syrup which was purified by column chromatography. Yield is generally low, but this is a quick method for preparing a representative sample of material for perfumery assessment.

Deprotection of the Ketal

The ketal was deprotected by the method as outlined for preparation route A.

Preparation Route C

Preparation of the Diseleoketal

Cyclododecanone (55 mmol) was dissolved in benzeneselenol (111 mmol) under a blanket of nitrogen. The resulting clear/colourless solution was purged with nitrogen for five minutes and then concentrated sulphuric acid (3 ml) was added in one portion (CAUTION: Exothermic, use a water bath to cool).

After 30 minutes the reaction was diluted with ether and washed with water, saturated sodium bicarbonate, water, and then dried with magnesium sulphate. The crude yellow/clear ethereal solution was added slowly to a suspension of lithium aluminium hydride (0.75 g) in ether at room temperature. Once this addition was complete a clear/colourless solution resulted. A solution of 50% aqueous potassium hydroxide was added dropwise until no further hydrogen evolution occured. The mixture was quickly filtered through celite under high vacuum, and the ethereal layer was then washed with aqueous sodium hydroxide (0.1M) twice, water, and then dried with magnesium sulphate, and evaporated invacuo to yield a low odour solid. Yield was 40%.
Reaction with Cyclohexane Dione-monoethyl Ketal The diselenoketal (21 mmol) was dissolved in anhydrous THF (yellow solution obtained) under nitrogen and cooled to −78° C. i-Butyl lithium (23 mmol) was added in one portion and the reaction mixture immediately went colourless. A yellow colouration began to appear after a few minutes which was very pronounced after ten minutes of stirring at −78° C. To this was then added the solid cyclohexane 1,4-dione monoethyleneketal (21 mmol) in one portion. The yellow colouration immediately disapeared, and the reaction mixture was left to warm to room temperature.

Once at room temperature the reaction was queanched with saturated aqueous ammonium chloride solution, extracted with ethyl acetate (×2). The combined organic fractions were washed with water (×3), dried (MgSO$_4$), and evaporated in vacuo. Purification by column chromatography yielded the desired product in a yield of 47%.
Formation of the Double Bond Using Trifluoroacetic Anhydride The α-hydroxyselenide (2.5 mmol) was dissolved in dichloromethane (10 ml) to which was then added triethylamnine (10 mmol), followed by trifluoroacetic anhydride (5 mmol). The resulting solution was left to stir at room temperature whilst being followed by TLC.

Once complete the reaction was quenched with saturated sodium bicarbonate, washed with water, dried with magnesium sulphate, and evaporated in vacuo. The residue that remained was purified by column chromatography to yield a colourless solid.
Preparation Route D The same as route A, but the ketone produced is then α-methylated under standard conditions.
Preparation Route E This molecule was obtained from an attempted deprotection of the ethylene glycol acetal of 4-octylidene-1-cyclohexanone with the palladium complex Pd(MeCN)$_2$Cl$_2$.

EXAMPLE 1

Preparation of Compound I (4-octylidene-1-cyclohexanone)

To a suspension of n-octyltriphenylphosphonium bromide (103 g, 0.226 mole) suspended in THF (500 ml) was added n-butyllithium (2.5M in hexanes, 100 ml, 0.249 mole) slowly dropwise keeping the temperature below 15° C. with ice cooling. During the course of this addition the white/colourless suspension slowly dissolves to yield a deep red/clear solution. Once the addition is complete the solution was left at room temperature for a further 30 minutes. After this time a solution of cyclohexane-1,4-dione monoethylene ketal (31.3 g, 0.204 mole) in THF (150 ml) is added slowly to the deep red solution. During the course of the addition the red colouration disappears to yield an orange solution containing a solid suspension. The temperature also increases to approximately 40° C. during the addition.

Once cooled to room temperature, water (150 ml) was added to dissolve the solid. The reaction mixture was shaken, and the organic layer was removed and concentrated in vacuo. The residue was partitioned between toluene (500 ml) and water (500 ml), and the toluene was further washed with brine (250 ml). The toluene was dried using a Dean and Stark, and then removed in vacuo to yield a viscous residue.

To the residue was added ether and the solid (triphenylphosphine oxide) that precipitated was removed by filtration, and further washed with ice-cold ether. The combined filtrates were evaporate in vacuo, and to the residue that remained was added ice-cold pentane. Again the solid that precipitated was removed by filtration, and washed with ice-cold pentane. The combined filtrates were evaporated in vacuo, and the residue that remained was distilled under reduced pressure.

The distillate from the Wittig reaction was poured into a mixture of concentrated HCl (160 ml) and butanone (40 ml), and shaken for a few minutes (until reaction complete by TLC). The solution was diluted with water (250 ml), and extracted twice with ether. The combined extracts were washed with water, saturated sodium bicarbonate, dried with magnesium sulphate, and concentrated in vacuo. The liquid residue remaining was distilled (B.p. 113–116° C./0.15 mmHg) to yield 18.9 g of an almost colourless liquid product. Overall yield was 18.9 g, 45% based on cyclohexane-1,4-dionemonoethylene ketal.

EXAMPLE 2

Preparation of Compound II (4-hexylidene-1-cyclohexanone)

To a suspension of n-hexyltriphenylphosphonium bromide (128 g, 0.300 mole) suspended in THF (500 ml) was added n-butyllithium (2.5M in hexanes, 126 ml, 0.315 mole) slowly dropwise keeping the temperature below 15° C. with ice cooling. During the course of this addition the white/colourless suspension slowly dissolves to yield a deep red/clear solution. Once the addition is complete the solution was left at room tempertureture for a further 30 minutes. After this time a solution of cyclohexane-1,4-dione monoethylene ketal (46.8 g, 0.300 mole) in THF (200 ml) is added slowly to the deep red solution. During the course of the addition the red colouration disappears to yield an orange solution containing a solid suspension. The temperature also increases to approximately 40° C. during the addition.

Once cooled to room temperature, water (200 ml) was added to dissolve the solid. The reaction mixture was shaken, and the organic layer was removed and concentrated in vacuo. The residue was partitioned between toluene (500 ml) and water (500 ml), and the toluene was further washed with brine (250 ml). The toluene was dried using a Dean and Stark, and then removed in vacuo to yield a viscous residue.

To the residue was added ether and the solid (triphenylphosphine oxide) that precipitated was removed by filtration, and further washed with ice-cold ether. The combined filtrates were evaporate in vacuo, and to the residue that remained was added ice-cold pentane. Again the solid that precipitated was removed by filtration, and washed with ice-cold pentane. The combined filtrates were evaporated in vacuo, and the residue that remained was distilled under reduced pressure (B.p. 106° C./0.4 mmHg) to yield 46 g of the ketal.

The distillate (46 g) from the Wittig reaction was poured into a mixture of concentrated HCl (320 ml) and butanone (80 ml), and shaken for a few minutes (until reaction complete by TLC). The solution was diluted with water (500 ml), and extracted twice with ether. The combined extracts were washed with water, saturated sodium bicarbonate, dried with magnesium sulphate, and concentrated in vacuo. The liquid residue remaining was distilled (86–88° C./0.4 mmHg) to yield an almost colourless liquid product. Overall yield of II was 24.3 g, 45% based on cyclohexane-1,4-dionemonoethylene ketal.

EXAMPLE 3

Preparation of Compound III (4(3-methylbutylidene)1-cyclohexanone)

To a suspension of isoamyl-triphenylphosphonium bromide (152 g, 0.368 mole) suspended in THF (500 ml) was added n-butyllithium (2.5M in hexanes, 160 ml, 0.400 mole) slowly dropwise keeping the temperature below 15° C. with ice cooling. During the course of this addition the white/colourless suspension slowly dissolves to yield a deep red/clear solution. Once the addition is complete the solution was left at room temperture for a further 30 minutes. After this time a solution of cyclohexane-1,4-dione monoethylene ketal (53.9 g, 0.350 mole) in THF (200 ml) is added slowly to the deep red solution. During the course of the addition the red colouration disappears to yield an orange solution containing a solid suspension. The temperature also increases to approximately 40° C. during the addition.

Once cooled to room temperature, water (200 ml) was added to dissolve the solid. The reaction mixture was shaken, and the organic layer was removed and concentrated in vacuo. The residue was partitioned between toluene (500 ml) and water (500 ml), and the toluene was further washed with brine (250 ml). The toluene was dried using a Dean and Stark, and then removed in vacuo to yield a viscous residue.

To the residue was added ether and the solid (triphenylphosphine oxide) that precipitated was removed by filtration, and further washed with ice-cold ether. The combined filtrates were evaporate in vacuo, and to the residue that remained was added ice-cold pentane. Again the solid that precipitated was removed by filtration, and washed with ice-cold pentane. The combined filtrates were evaporated in vacuo, and the residue that remained was distilled under reduced pressure.

The distillate from the Wittig reaction was poured into a mixture of concentrated HCl (320 ml) and butanone (80 ml), and shaken for a few minutes (until reaction complete by TLC). The solution was diluted with water (500 ml), and extracted twice with ether. The combined extracts were washed with water, saturated sodium bicarbonate, dried with magnesium sulphate, and concentrated in vacuo. The liquid residue remaining was distilled (82–84° C./0.4 mmHg) to yield an almost colourless liquid product. Overall yield of III was 18.4 g, 30% based on cyclohexane-1,4-dionemonoethylene ketal.

What is claimed is:

1. A cyclic ketone having the structure

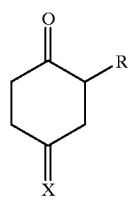

in which R is H or an alkyl group and X is a hydrocarbon group having between 4 and 12 carbon atoms, the ring structure shown being saturated or mono-unsaturated, excluding 4-(1-ethylpropylidene)-1-cyclohexanone, 4-cyclohexylidene-1-cyclohexanone, 4-butylidene-1-cyclohex-2-enone, 4-(1-ethylpropylidene)-1-cyclohex-2-enone, 4-(2- methylpropylidene)-1-cyclohexanone, 4-cyclohexyliden-2-cyclohexen-1-one, 4(1,5- dimethyl-4-hexenylidene)-1-cyclohexanone, 4-[-cyclohexyliden) cyclohexyliden]-1- cyclohexanone, 4-[4-(tert-butyl) cyclohexyliden]-1-cyclohexanone, 4-[4- (cyclohexyl) cyclohexyliden]-1-cyclohexanone, 4-(2-isopropyl-5-methylcyclohexyliden)- 2-cyclohexen-1-one and 4-(3-phenylpropylidene)-1-cyclohex-2-enone.

2. A cyclic ketone having the structure

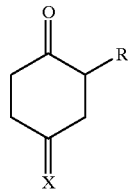

in which R is H or an alkyl group and X is a hydrocarbon group having between 4 and 12 carbon atoms, the ring in the structure shown being saturated or mono-unsaturated, the ketone having fragrance properties.

3. A cyclic ketone according to claim 1, wherein X is a saturated straight chain group.

4. A cyclic ketone according to claim 1, wherein X has 6 or 8 carbon atoms.

5. A cyclic ketone according to claim 1, wherein R is H or a lower alkyl group.

6. A cyclic ketone according to claim 1, having a total of 18 or less carbon atoms.

7. A cyclic ketone having the structure

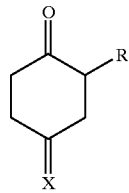

in which R is H, the cyclic ketone is saturated and X is a straight chain hydrocarbon chain having 6 or 8 carbon atoms.

8. A ketone having the structure

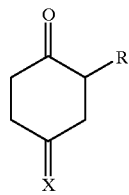

in which R is H, the cyclic ketone is saturated and X is an iso-amyl chain attached to the cyclic ketone by a double bond.

9. A perfume according to claim 1, wherein the ketone is present in an amount of at least 0.01% by weight.

10. A perfume according to claim 1, wherein the ketone is present in an amount in the range 0.1 to 80% by weight.

11. A perfumed product comprising a cyclic ketone according to claim 1.

* * * * *